United States Patent [19]

Somlyai

[11] Patent Number: 5,788,953
[45] Date of Patent: Aug. 4, 1998

[54] HYGIENIC AND COSMETIC PREPARATIONS FOR PREVENTING AND TREATING SKIN-DISEASES AS WELL AS A PROCESS FOR OBTAINING SAME

[75] Inventor: Gábor Somlyai, Budapest, Hungary

[73] Assignee: HYD Kutato-Fejleszto Kft., Budapest, Hungary

[21] Appl. No.: 714,109

[22] PCT Filed: Mar. 23, 1995

[86] PCT No.: PCT/HU95/00007

§ 371 Date: Sep. 23, 1996

§ 102(e) Date: Sep. 23, 1996

[87] PCT Pub. No.: WO95/25526

PCT Pub. Date: Sep. 28, 1995

[30] Foreign Application Priority Data

Mar. 23, 1994 [HU] Hungary .................. P 94 00833

[51] Int. Cl.⁶ ........................................... A61K 7/42
[52] U.S. Cl. ........................... 424/59; 424/65; 424/70.1
[58] Field of Search ........................... 424/59, 65, 70.1

[56] References Cited

FOREIGN PATENT DOCUMENTS

93/08794  5/1993  WIPO.

Primary Examiner—James H. Reamer
Assistant Examiner—Dwayne C. Jones
Attorney, Agent, or Firm—Keil & Weinkauf

[57] ABSTRACT

The invention relates to hygienic and cosmetic preparations for preventing and treating skin diseases, including beauty and body care products, comprising water having a lowered deuterium content of 111 to 135 ppm. The hygienic and cosmetic preparations according to the invention are capable of preventing and treating a broad spectrum of skin diseases.

9 Claims, No Drawings

HYGIENIC AND COSMETIC PREPARATIONS FOR PREVENTING AND TREATING SKIN-DISEASES AS WELL AS A PROCESS FOR OBTAINING SAME

This application is a 371 of PCT/HU95/00007.

BACKGROUND OF THE INVENTION

The present invention relates to hygienic and cosmetic preparations for preventing and treating skin-diseases, including beauty and body-care products, and to a process for obtaining such preparations.

The incidence of cancerous skin-diseases, as is well-known, has suddenly increased in the last years, because the ozone layer surrounding the earth has been growing thin. In the future this tendency seems to be even more significant, since the measures taken nowadays all over the world proved to be insufficient even for maintaining the ozone layer in the present state. This raises the question: how to prevent the development of cancerous skin-diseases.

The increasing number of cancerous skin-diseases due to the thinner ozone layer can be traced back to rising UV doses on the earth surface. Having a strong mutagenic activity, UV radiation can induce genetic mutations in the skin-surface exposed to this radiation. If these genetic mutations take place in the genes playing an important role in the cell cycle regulation, it can significantly increase the possibility of malignant transformations.

There is hardly anyone who has no pigmented birthmarks on the skin-surface. These birthmarks cannot be regarded as malignant tumours, but a malignant transformation can be initiated therein, for example by UV radiation. The solution of this problem seemed to be the preventive ablation of these birthmarks, still at rest, from the skin. This conception, however, proved to be unrealizable, since the operative treatments ought to be extended practically to the whole population of most countries.

Considering that the cancerous skin-diseases belong to the most malignant tumourous diseases, the prevention in this field is of extreme importance. If a perfect ablation of the cancerous parts before spreading the touched cells failed at the first operation, the diseases of this kind turn incurable.

The aim of the present invention is to provide hygienics and cosmetics of therapeutical activity, which make the prevention of cancerous skin-diseases possible by promoting a selection of malignant cells originating from mutations caused for example by UV radiation, just before these cells become numerous enough to create tumours. A further aim of the invention is to provide beauty and body-care products comprising deuterium-depleted water (Dd-water) for retarding ageing processes and treating simpler cutaneous lesions or diseases.

The invention is based on the recognition that unfavourable conditions for the malignant cells can be created and the formation of tumours can be prevented by decreasing locally and temporarily the deuterium content of the water in the upper skin-layer. We have namely discovered that cell-division is triggered by increasing the relative D/H concentration ratio as an element of a submolecular regulation system. The deuterium present in the organism is essential particularly for the tumourous cells having a high proliferation rate.

A further basis of the invention is the recognition that by using water-based cosmetics of decreased (111–135 ppm) deuterium content, the deuterium concentration of the skin is also decreased due to exchange processes. For this reason the preparations with decreased deuterium content are capable of stopping the division of tumourous cells and preventing in this way tumour formation. These preparations therefore can be used for preventing and treating tumourous diseases, for retarding ageing processes in the skin and for treating other skin-diseases, for example psoriasis.

DETAILED DESCRIPTION OF THE INVENTION

In accordance with the above-mentioned facts, the invention relates to hygienic and cosmetic preparations of therapeutical activity, including beauty and body-care products, comprising deuterium in an amount of from 111 to 135 ppm, preferably from 111 to 128 ppm, more preferably from 111 to 118 ppm. The preparations according to the invention are capable of preventing and treating skin-diseases such as psoriasis and shingles (herpes zoster).

The preparations according to the invention are hygienic and cosmetic products including beauty and body-care preparations such as creams, ointments, emulsions, jellies, suspensions, tonics, suncreams, after-sunbath preparations, dentifrices, mouth-washes, hand- and hair-care products, after-shaves, muscle-relaxant creams, ointments and tonics for sporting, shaving and hair cosmetics, antiperspirants, skin-protecting products, liposome preparations, cosmetics for skiing and sun-bathing, baby-care cosmetics, etc. and concentrates of these products.

The invention relates also to a process for manufacturing these preparations. According to this process water containing 111 to 135 ppm, preferably 111 to 128 ppm, more preferably 111 to 118 ppm, of deuterium is used by methods conventionally applied in the cosmetic industry for preparing hygienic and cosmetic products.

Deuterium-depleted water can be produced by using a) electrolysis or b) distillation procedures, preferably in the following way:

a) Aqueous 15–20 w/v % KOH solution is electrolyzed by direct current at a voltage of 2 to 5 V in an electrolyzer equipped with a cathode and an anode separated from each other. Hydrogen evolving with low deuterium content at the cathode is burnt and the so-obtained steam is condensed and separately collected. This procedure gives water with a deuterium concentration of 30 to 40 ppm (Isotope Separation, Eds.: Stelio Villani, American Nuclear Society, 1983) which is mixed with normal water containing 150 ppm of deuterium. Water having decreased deuterium content of 111 to 135 ppm can be prepared by mixing normal water and Dd-water produced as described above in different proportions.

b) The water is distilled in a fractionating column of 30–50 plates under a pressure of 5–6 kPa at a temperature of 45° to 50° C. Maintaining reflux at a value of 12 to 13 and tenfold water output from the still pot in the course of the distillation procedure, water having a deuterium content of 20 to 30 ppm can be produced as head product (Separation of Hydrogen Isotopes, Eds.: Howard K. Rae, American Chemical Society Symposium Series 68, Washington, D.C., 1978).

Due to their decreased content in deuterium, the preparations produced according to the invention are capable of preventing cancerous skin-diseases by decreasing the deuterium concentration in the skin. As a result of this concentration the proliferation of tumourous cells is slowed down, then the tumourous cells die.

Completing a series of toxicological tests, ingestion of water of low deuterium content proved to be harmless, therefore the preparations according to the invention could be tested on human beings, too.

The case reports on 88 tumourous patients proved the effectiveness of the Dd-water-based preparations within a 2-year long period. In these cases tumours on the skin surface or near to this surface were treated and in 83 cases unambiguous improvement was observed.

From our test results the following are separately mentioned:

a) Antitumourous effects

There was a lesion of melanoma character on the forehead of a male patient, which had not been healing for a long time. As results of using regularly a water-based gel containing water of low deuterium content for 8 months, the scab on the skin-lesion rising from the skin-surface became repeatedly detached, the remaining wound surfaces were getting more and more smaller, the skin-lesion was more and more flat and at the end but a hollowness was left. A solid tumour of fair prospects was histologically diagnosed 2 months later.

A female patient applied a water-based gel containing water of low deuterium concentration to a knot (nodus) remaining after melanocarcinectomy at the inguinal region. The knot became more and more softer in the course of the treatment, and the patient has been living symptomless and free from complaints for more than two years.

A gel with low deuterium content was applied by 18 female patients having breast tumour. Some of the patients applied the gel preparation to recidivistic tumours formed in the breast near to the skin-surface. Other patients suffering from subcutaneous metastases were treated with the mentioned gel. The tumours became in each case softer and smaller within a few days or 1–2 weeks.

The preparations according to the invention proved to be effective at treating other primary tumours and metastases formed near to the skin-surface, for example in the larynx or in the tongue.

b) Effects on Non-tumourous Skin-diseases

A male patient applied the mentioned Dd-water-based gel to his psoriasis spread over the whole body surface. The skin-surface infected with psoriasis was significantly decreased in 3 months and some further months there were no more symptomps e.g. on his right arm.

On treating blackburry-like fibroma of a female patient the size of the fibroma was significantly decreased in some weeks.

Influencing strongly pigmented skin-surfaces of 3 patients, a Dd-water-based hydrating gel decreased the pigmentation level.

A Dd-water-based cream removed warts from face-skin.

Incurable skin-tuberculosis of a 10-year history was healed in 4 weeks by using a preparation according to the invention.

c) Antiageing effects

A double blind experiment involving 30 persons was effected to find out whether the Dd-water-based preparations had wrinkle-removing activity. One cheek of the participants in the experiment was smeared with a normal water-based hydro-gel and the other cheek was treated in the same way with a Dd-water-based gel for 3 weeks. After the treatment it could be unambiguously ascertained which one of the two cheeks was treated with the gel according to the invention, since the fine wrinkles around the eyes disappeared only from this face halves. The Dd-water-based hydrating gel had smoothed out the surface wrinkles in initial stage and the skin became more young-looking and stretched.

The main advantages of the preparations according to the invention, including also the beauty and body care preparations, are as follows:

a) The preparations according to the invention, at using them locally on the skin-surface, intervene in the regulation mechanism of the malignant cells resulting in stopping the cell division and giving a chance for the organism to eliminate the potential tumour formations.

b) They make possible the prevention of the tumourous diseases since they create conditions unfavourable for proliferation of malignant cells.

c) They have no toxic side-effects.

d) Since Dd-water is not mutagenic, the preparations do not induce mutant cells in the course of the treatment.

e) Due to their general therapeutical mechanism, the preparations are capable of preventing and treating a broad spectrum of skin-diseases.

f) They can be produced in a simple way.

g) No wastes dangerous to the environment originate from the production of the preparations according to the invention.

The product and process according to the invention are illustrated in more detail in the following formulation examples, without limiting the scope claimed. The preparations according to the examples are formulated by methods conventionally used in the cosmetic industry.

The compositions according to the examples can be completed with sunscreen factors, flavours and potentiators, such as vitamins, humic acids, trace elements, alfa-hydroxy-derivatives of fruit acids, enzymes, coenzymes, royal jelly, propolis, plant extracts containing elastin and collagen, D-panthenol, etc.

EXAMPLES

Example 1

Hydrating Cream of Gel Consistency

| | |
|---|---|
| Carbopol 1342 (Goodrich, Cleveland) | 0, 2 g |
| Emulsifying agent (Dragoco, Vienna) | 0, 3 g |
| Glycerol | 2 g |
| Triethanolamine (pH = 5, 5) | 0, 2 g |
| Ceraderm complex (Dragoco, Vienna) | 6, 0 g |
| Dd-water | 91, 3 g |

Example 2

Face-cream with Glycerol Content

| | |
|---|---|
| Glycerol | 3 g |
| Preserving agent (ISP, Delaware) | 0, 8 g |
| Carbopol 934 (Goodrich, Cleveland) | 0, 25 g |
| Emulsifying agent o/v (Dragoco, Vienna) | 2, 7 g |
| Plant extract (Dragoco, Vienna) | 0, 5 g |
| Mixture of cetyl alcohol and stearyl alcohol (Henkel, Düsseldorf) | 2 g |
| Vegetable oils (Dragoco, Vienna) | 8 g |
| Vitamin complex (Dragoco, Vienna) | 5 g |
| Flavour | 0, 2 g |
| Vaseline (Neuber, Vienna) | 3 g |
| Dd-water | 67, 55 g |

Example 3

Suncream of Factor 10

| | |
|---|---|
| Eusolex 6300 (Merck, Darmstadt) | 1, 5 g |
| Arlacel 581 (ICI, Essen) | 6, 0 g |
| Paraffin oil | 14, 5 g |
| Beeswax (cleaned) | 3, 0 g |
| Mygliol 812 (Hüls Troisdorf AG, Witten) | 11, 5 g |
| Dow Corning 200 (Dow Corning, Düsseldorf) | 2, 0 g |
| Tocopherole acetate (Merck, Darmstadt) | 0, 5 g |
| Eusolex TA (Merck, Darmstadt) | 5, 0 g |
| Glycerol | 2, 0 g |
| Magnesium sulfate heptahydrate (Merck, Darmstadt) | 0, 7 g |
| Dd-water | 53, 3 g |

Example 4

Body Lotion with Skin-stress Releasing Effect

| | |
|---|---|
| Cremophor A6 (BASF, Leverkusen) | 2, 0 g |
| Cremophor A 25 (BASF, Leverkusen) | 2, 0 g |
| Luvitol EHO (Henkel, Düsseldorf) | 7, 0 g |
| Paraffin oil | 8, 0 g |
| Glycerol monostearate | 6, 0 g |
| Tegiloxan 100 (Goldschmidt, Essen) | 0, 2 g |
| alpha-Bisabolol (Henkel, Dusseldorf) | 0, 2 g |
| D-Panthenol (Merck, Darmstadt) | 1, 0 g |
| 1,2-Propanediol (Merck, Darmstadt) | 3, 0 g |
| Dd-water | 70, 6 g |

This product can be used as after-sunbath balm, too.

Example 5

Face-tonic

| | |
|---|---|
| Glycerol (Neuber, Vienna) | 5, 0 g |
| Emulsifying agent (Dragoco, Vienna) | 0, 3 g |
| Ethanol (96 % by v.) | 1, 0 g |
| Neo PCL liquid (Dragoco, Vienna) | 1, 0 g |
| Flavour | 0, 2 g |
| AHA fruit acid complex (Dragoco, Vienna) | 5 g |
| Dd-water | 79, 7 g |

Example 6

Baby Care Product

| | |
|---|---|
| Ceteareth-6 (stearyl alcohol) (BASF, Leverkusen) | 2 g |
| Cetearyl octanoate (BASF, Leverkusen) | 10 g |
| Paraffin oil | 10 g |
| alpha-Bisabolol (Dragoco, Vienna) | 0, 3 g |
| 1,2-Propanediol (Shell, London) | 3 g |
| Carbopol 934 (Goodrich, Cleveland) | 20 g |
| Triethanolamine HCl | 0, 3 g |
| Dd-water | 54, 4 g |

Example 7

Hand Care Balm

| | |
|---|---|
| Teginacid H (Goldschmidt, Vienna) | 2 g |
| Emulsifying agent (Goldschmidt, Vienna) | 1 g |
| Mixture of cetyl alcohol and stearyl alcohol (Henkel, Düsseldorf) | 1, 5 g |
| Cold-pressed vegetable oils | 6–13 g |
| Plant extract (Dragoco, Vienna) | 1 g |
| Hydroviton (Dragoco, Vienna) | 0, 6 g |
| Flavour | 0, 2 g |
| Preserving agent (ISP, Delaware) | 0, 3 g |
| Glycerol | 1 g |
| Dd-water | 79, 4–86, 4 g |

Example 8

Shaving Foam

| | |
|---|---|
| Stearic acid | 3, 78 g |
| Myristic acid | 3, 06 g |
| Triethanolamine HCl | 3, 33 g |
| Propyleneglycol (Neuber, Vienna) | 2, 16 g |
| PCL liquid (Dragoco, Vienna) | 0, 54 g |
| Flavour | 0, 27 g |
| Menthol (Neuber, Vienna) | 0, 1 g |
| Lanolin (Henkel, Düsseldorf) | 0, 45 g |
| Ungerol LES 70 (Unger, Fredrikstad) | 1, 4 g |
| Isobutane (Hunsett) | 5, 0 g |
| Dd-water | 79, 91 g |

Example 9

After-shave (without Alcohol)

| | |
|---|---|
| Bisabolol (BASF, Leverkusen) | 0, 2 g |
| PEG-40 (ICI, Everberg) | 2, 0 g |
| Luwiquat Mono CP (BASF, Leverkusen) | 1, 0 g |
| Flavour IFF (Dragoco, Vienna) | 0, 3 g |
| Methyl lactate (Hungaropharma, Budapest) | 0, 1 g |
| Propyleneglycol (Neuber, Vienna) | 2, 0 g |
| Preserving agent (ISP, Delaware) | 0, 1 g |

Example 10

Foot Care Cream

| | |
|---|---|
| Teginacid (Goldschmidt, Essen) | 2, 0 g |
| Emulsifying agent (Goldschmidt, Essen) | 2, 0 g |
| Mixture of cetyl alcohol and stearyl alcohol (Henkel, Düsseldorf) | 3, 0 g |
| Stearic acid (Neuber, Vienna) | 2, 0 g |
| White oil | 4, 0 g |
| Glycerol (Neuber, Vienna) | 1 g |
| Ethereal oils (Dragoco, Vienna) | 6, 0 g |
| Menthol (Neuber, Vienna) | 0, 1 g |
| Vitamin (Dragovit F) (Dragoco, Vienna) | 1 g |
| Preserving agent (ISP, Delaware) | 0, 2 g |
| Ethyl alcohol (96% by v.) | 1, 6 g |
| Dd-water | 74, 1 g |

Example 11

Antiscurf Medicinal Shampoo

| | |
|---|---|
| Ungerol LES 370 (Unger, Fredrikstad) | 18, 0 g |
| Zalabetain R35 (Caola, Budapest) | 5, 0 g |
| Alfid D 11 (Caola, Budapest) | 1, 0 g |
| Propyleneglycol (Neuber, Vienna) | 1, 5 g |
| Flavour (Dragoco, Vienna) | 0, 8 g |
| Preserving agent (ISP, Delaware) | 0, 1 g |
| Herb extract (Dragoco, Vienna) | 1, 03 g |
| Dd-water | 72, 57 g |

Example 12

Mouth-wash with Antiphlogistic Effect

| | |
|---|---|
| Texapon K 12 (Henkel, Düsseldorf) | 5, 0 g |
| Cremogen chamomile (Dragoco, Vienna) | 0, 5 g |
| Cremogen Hamamelis (Dragoco, Vienna) | 5, 0 g |
| Arnica tincture (Dragoco, Vienna) | 5, 0 g |
| Menthol (Neuber, Vienna) | 0, 2 g |
| Thymol (Merck, Darmstadt) | 0, 5 g |
| Aroma (Dragoco, Vienna) | 1, 5 g |
| Ethyl alcohol (96% by v.) | 10, 0 g |
| Dd-water | 71, 3 g |

I claim:

1. Hygienic and cosmetic preparations for preventing and treating skin-diseases, including beauty and body-care products, comprising water having a lowered deuterium content of 111 to 135 ppm.

2. Preparations as claimed in claim 1, comprising water having a deuterium content of 111 to 128 ppm.

3. Preparations as claimed in claim 1, characterized in that they comprise water having a deuterium content of 111 to 118 ppm.

4. Preparations as defined in any of claims 1 to 3, formulated as creams, ointments, emulsions, jellies, suspensions, tonics, sun-creams, after sun-bath preparations, dentifrices, mouth-washes, hand- or hair-care products, after-shaves, muscle-relaxant creams, ointments or tonics for sporting, shaving or hair cosmetics, antiperspirants, skin-protecting products, liposome preparations, cosmetics for skiing or sunbathing, baby-care cosmetics, or concentrates of these products.

5. A process for obtaining the preparations as claimed in claim 1, in which water having a deuterium content of 111 to 135 ppm is used in procedures conventionally applied in the cosmetic industry.

6. The process as claimed in claim 5, in which water having a deuterium content of 111 to 128 ppm is used.

7. The process as claimed in claim 5, in which water having a deuterium content of 111 to 118 ppm is used.

8. The process of claim 5, in which creams, ointments, emulsions, jellies, suspensions, tonics, sun-creams, after sun-bath preparations, dentifrices, mouth-washes, hand- or hair-care products, after-shaves, muscle-relaxant creams, ointments or tonics for sporting, shaving or hair cosmetics, antiperspirants, skin-protecting products, liposome preparations, cosmetics for skiing or sunbathing, baby-care cosmetics, or concentrates of these products are produced.

9. A process for preventing or treating skin-diseases comprising applying to the skin a hygienic or cosmetic preparation containing deuterium-depleted water having a deuterium content of 111 to 135 ppm.

* * * * *